(12) United States Patent
McBride

(10) Patent No.: US 6,395,232 B1
(45) Date of Patent: May 28, 2002

(54) FLUID DELIVERY SYSTEM FOR A MICROFLUIDIC DEVICE USING A PRESSURE PULSE

(75) Inventor: Sterling Eduard McBride, Lawrenceville, NJ (US)

(73) Assignee: Orchid BioSciences, Inc., Princeton, NJ (US)

(*) Notice: Subject to any disclaimer, the term of this patent is extended or adjusted under 35 U.S.C. 154(b) by 0 days.

(21) Appl. No.: 09/351,206

(22) Filed: Jul. 9, 1999

(51) Int. Cl.[7] ................................. B01L 3/02
(52) U.S. Cl. .................. 422/100; 422/100; 422/102; 435/286.5
(58) Field of Search ................ 422/102, 100; 204/603, 269; 435/286.5; 347/12, 13; 436/173, 514

(56) References Cited

U.S. PATENT DOCUMENTS

| | | | |
|---|---|---|---|
| 4,390,885 A | * | 6/1983 | Shah et al. |
| 4,676,274 A | | 6/1987 | Brown |
| 5,240,578 A | | 8/1993 | Tatsumi |
| 5,302,264 A | | 4/1994 | Welch |
| 5,310,463 A | | 5/1994 | Dadoo |
| 5,578,179 A | | 11/1996 | Demorest |
| 5,597,468 A | | 1/1997 | Lauer |
| 5,726,404 A | | 3/1998 | Brody |
| 5,801,951 A | * | 9/1998 | Burns et al. |
| 5,856,174 A | * | 1/1999 | Lipshutz et al. |
| 5,872,010 A | * | 2/1999 | Karger et al. |
| 5,879,632 A | * | 3/1999 | Demers |
| 5,942,443 A | * | 8/1999 | Parce et al. |
| 5,980,704 A | * | 11/1999 | Cherukuri et al. |
| 6,033,546 A | * | 3/2000 | Ramsey |
| 6,117,396 A | * | 9/2000 | Demers |
| 6,136,212 A | * | 10/2000 | Mastrangelo et al. |

FOREIGN PATENT DOCUMENTS

EP     0 733 905 A2 *  9/1996

* cited by examiner

*Primary Examiner*—Jill Warden
*Assistant Examiner*—Brian J. Sines
(74) *Attorney, Agent, or Firm*—Kevin G. Mierzwa

(57) ABSTRACT

A microfluidic fluid delivery system includes a microfluidic device having a fluid input. A fluid reservoir is fluidically coupled to the fluid input. A gas delivery system has a pulse generator that generates an electric pulse. An electrically operated valve is coupled to the pulse generator and the gas pressure source. The valve controls the gas pressure pulse in response to said electric pulse. The gas pressure pulse displaces fluid from the fluid reservoir into the plurality of capillaries.

19 Claims, 3 Drawing Sheets

FLUID DELIVERY SYSTEM FOR A MICROFLUIDIC DEVICE USING A PRESSURE PULSE

RELATED APPLICATION

This application is related to co-pending U.S. patent application Ser. No. 09/349,438 entitled "Fluid Delivery System for A Microfluidic Device Using Alternating Pressure Pulses filed simultaneously with the present application, the subject matter of such co-pending application being incorporated herein by reference.

TECHNICAL FIELD

The present invention relates to microfluidic devices, and more particularly, to a method and apparatus for distributing fluid on a microfluidic device.

BACKGROUND OF THE INVENTION

Methods of making a homologous series of compounds, or the testing of new potential drug compounds comprising a series of light compounds, has been a slow process because each member of a series or each potential drug must be made individually and tested individually. For example, a plurality of potential drug compounds is tested by an agent to test a plurality of materials that differ perhaps only by a single amino acid or nucleotide base, or a different sequence of amino acids or nucleotides.

The processes described above have been improved by microfluidic chips which are able to separate materials in a microchannel and move the materials through the microchannel is possible. Moving the materials through microchannels is possible by use of various electro-kinetic processes such as electrophoresis or electro-osmosis. Fluids may be propelled through various small channels by the electro-osmotic forces. An electro-osmotic force is built up in the channel via surface charge buildup by means of an external voltage that can repel fluidly and cause flow.

Another method for the movement of fluids is the use of an electrohydrodynamic pump. In electro-osmotic and electrohydrodynamic pumping, electrodes are placed within the microfluidic structure.

In fluid delivery in microfluidic structures, it is important to distribute approximately the same fluid volume to each reaction well. In using certain fluids, however, even distribution within reaction wells is difficult to accomplish.

SUMMARY OF THE INVENTION

It is, therefore, one object of the invention to provide an improved fluid delivery mechanism to an array of reaction wells. It is a further object of the invention to provide a reliable method for delivering fluid to reaction wells.

It is another object of the present invention to create a relatively small device which can carry out hundreds and even thousands of chemical experiments simultaneously, create new compounds, and measure their reactivities.

It is yet another object of the present invention to provide a liquid handling drug discovery and diagnostic tool which increases the speed and productivity of discovering new drug candidates and does so on a miniaturized, scale or platform that reduces cost and manual handling. It is still a further object of the present invention to provide a multiple fluid sample processor, system and method which is capable of conveying, transporting, and/or processing samples in a large multiplicity of sites without exposure to the atmosphere.

In one aspect of the invention, a microfluidic fluid delivery system includes a microfluidic device having a fluid input. A fluid reservoir is fluidically coupled to the fluid input. A gas delivery system has a pulse generator that generates an electric pulse. An electrically operated valve is coupled to the pulse generator and the gas pressure source. The valve controls the gas pressure pulse in response to said electric pulse. The gas pressure pulse displaces fluid from the fluid reservoir into the plurality of capillaries.

In a further aspect of the invention, a method of distributing fluid to a microfluidic chip comprises the steps of: providing a reservoir having fluid therein; pressurizing the fluid at a first pressure; filling the channel in the microfluidic device until the channel is filled to the capillary break; generating a pressure pulse; and thereby, displacing fluid from the reservoir in response to the pressure pulse.

One advantage of the invention is that small and controlled amounts of fluid may be delivered in an array structure with microchannels that have high pressure losses. Another advantage of the invention is that the method for delivering fluid to microfluidic structures is applicable to structures having high integration densities and where viscous losses in micro channels are significant.

Other objects and features of the present invention will become apparent when viewed in light of the detailed description of the preferred embodiment when taken in conjunction with the attached drawings and appended claims.

DETAILED DESCRIPTION OF THE PREFERRED EMBODIMENT

Figure 1:
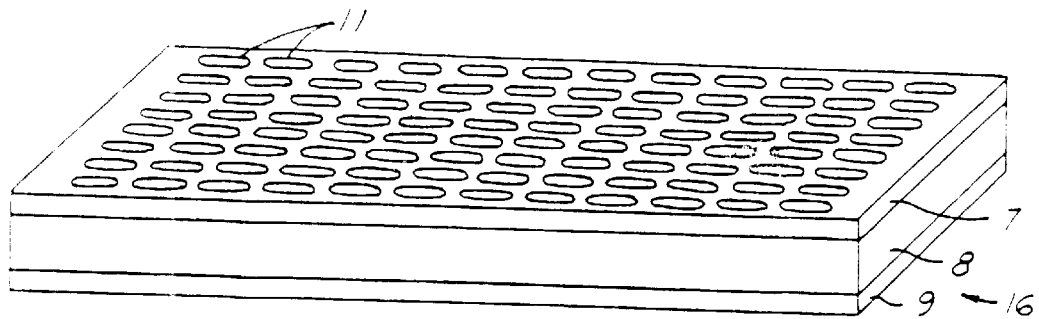
FIG. 1 illustrates a multiple fluid sample processor according to the present invention.

Referring now to the drawings, like reference numerals are used to identify identical components in the various views. The present invention can be used particularly in the industrialization of drug discovery processes. The present invention increases speed and productivity while providing researchers with expanded capabilities and assuring quality. The invention provides substantial time and efficiency advantages over prior techniques. The invention provides miniaturized liquid handling systems which perform the biological, chemical and the analytical processes fundamental to life sciences, research and development. The invention can be utilized to perform thousands of reactions simultaneously in an integrated format, which substantially reduces the time, effort and expense required while improving the quality of the test results.

The processor in accordance with the present invention generally incorporates a modular configuration with distinct layers or plates. The processor or microfluidic device 16 is capable of conducting parallel synthesis of thousands of small molecule compounds through the precise delivery of reagents to discrete reaction sites. This helps create a significantly larger number and variety of small molecules more effectively and with fewer resources.

With the present invention, arrays of DNA can be synthesized on demands. The processor can also be used for high volume of sample processing and testing, as well as the search for new molecular targets and determining expression levels and response to known drugs The processor can incorporate multiple assay formats, such as receptor binding, antibody-antigen interactions, DNA/RNA amplification and detection, as well as magnetic deed base separations. The versatility of the processor and its architecture make it available for use with synthesizer work stations, genomic support stations, and analytical preparation systems.

Figure 2:
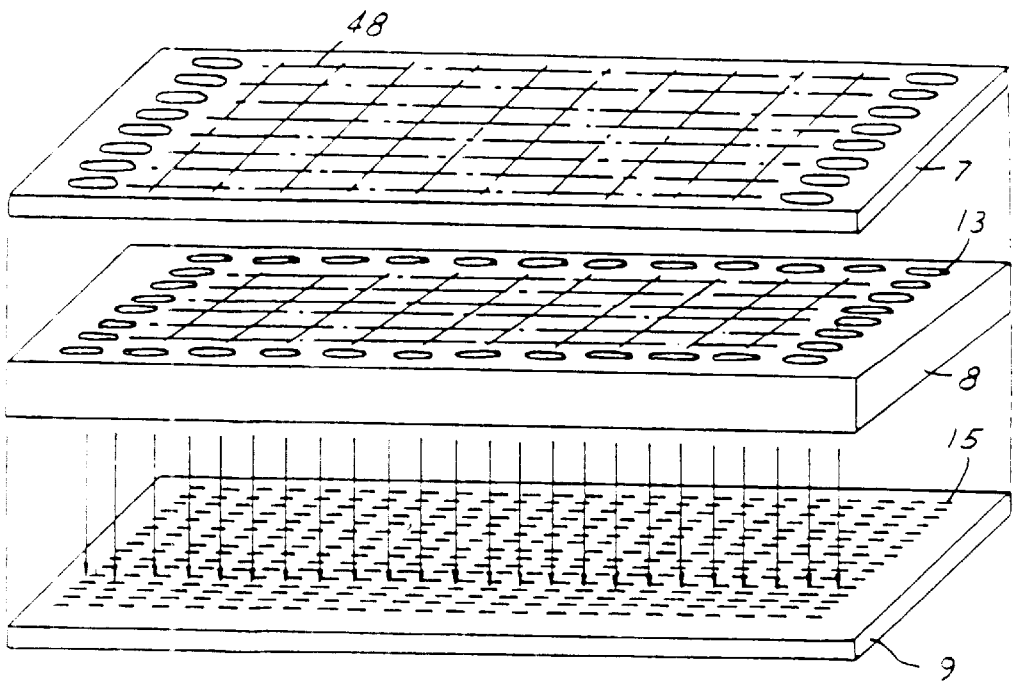
FIG. 2 is an exploded view of the processor shown in FIG. 1.

A basic multiple fluid sample processor or microfluidic device 16 in accordance with the present invention is shown in FIGS. 1 and 2, with cross-sections of the layers being shown in FIGS. 5, 6, 7 and 8. The microfluidic device is illustrated as a three-layered structure in the embodiment illustrated. The microfluidic device 16 is also called a fluid assay layered device (FALD), or a fluidic array.

The microfluidic device 16 includes a top layer 7, which is also called a reagent reservoir. The microfluidic device 16 also includes a middle layer or fluidic delivery layer 8, as well as a bottom layer or well plate 9.

The top layer 7 is also called a feed-through plate and serves as a cover for the microfluidic device 16. Layer 7 contains a number of apertures 11 which are selectively positioned immediately above apertures 13 in layer 8. Apertures 13 are connected by an elongated micro-channel 48 which in turn have a plurality of branches extending therefrom. As illustrated, layer 8 contains one layer, however, one skilled in the art would recognize that layer 8 may comprise several layers.

Well plate 9 has a plurality of wells 15 which are used to hold the reagents and other materials in order for them to react and synthesize.

The three layers 7, 8 and 9 are stacked together to form a modular configuration. They are also coupled together tightly to form a liquid-tight seal. If desired, the top layer 7 can be bounded or fused to the center distribution plate 8 or layer. The bottom or well plate Layer 9, however, is detachably coupled to layer 8.

The plates 7, 8 and 9 may be made from any desirable material, such as glass, fused silica, quartz, or silicon wafer material. The reservoirs, micro-channels and reaction cells are controllably etched or otherwise formed onto the plates using traditional semi-conductor fabrication techniques with a suitable chemical etchant or laser drilling, reactive in etching.

Top plate 7 contains apertures positioned above the openings 13 located in the central plate. These apertures provide the necessary openings for loading module to fill the reservoirs with a plurality of agents or other materials.

As will be further described below, a pressure pumping mechanism, is preferably used to assist in loading and distributing the reagents and other materials within the layers.

A typical need is for one of the sample plates to have each sample repeatedly conveyed, transported and/or processed while eventually being delivered into the well plate. During this time, the samples are typically exposed to the atmosphere and can oxidize, evaporate or cross-contaminate to an undesirable extent. With the present invention, however, the multi-layered sample microfluidic device 16 with detachable well plates inhibits cross-contamination of the fluids used in the combinatorial process.

The detachable layers in accordance with the present invention are preferably of a common dimensionality for ease of being handled by robotic or other automation means. A common set of dimensions has been adopted by many manufacturers which match that of the 96-well plate known as a "micro titer" plate.

Preferably, the plates 7, 8 and 9 are connected to each other by an indexing means of detents, flanges or locating pins so they are closely aligned in the horizontal and vertical directions. While engaged in such manner, samples from one of the plates can be caused to be moved and transported to another plate. Means for transporting or moving the samples from one of the plates to the other can be by pumping, draining, or capillary action. While the samples are engaged, and as a result of the transport of the samples from one layer to the other, the samples may be processed, reacted, separated, or otherwise modified by chemical or physical means, and then finalized by optical, electrochemical, chemical, or other means.

Samples or fluids can be delivered to the microfluidic device 16 by being contained in one of the members of physically engaging sample multi-well plates, such as a top layer 7, or other means of sample introduction can be utilized, such as through the edges of such layer.

Figure 3:
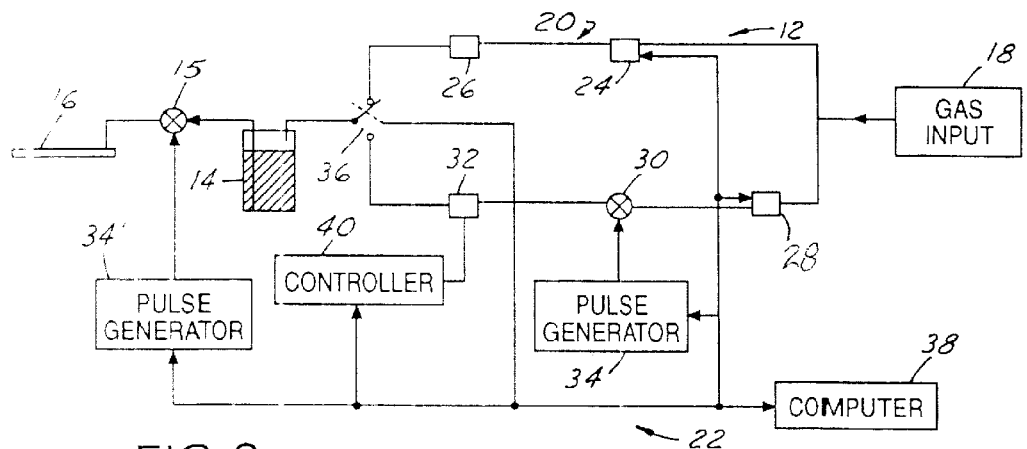
FIG. 3 is a block diagram schematic view of a microfluidic fluid delivery system according to the present invention.

Referring now to FIG. 3, microfluidic fluid distribution system 10 is shown having a gas delivery system 12 coupled to a fluid reservoir 14. Fluid reservoir 14 is fluidically coupled to a microfluidic device 16 through a valve 15. In general, gas delivery system 12 is used to displace fluid from fluid reservoir 14 into microfluidic device 16.

Gas delivery system 12 has a gas input 18. The gas in gas input 18 should not be reactive with reagents in the microfluidic device 16. For example, for many applications, nitrogen is a suitable gas. Gas input 18 provides a high-pressure source of gas to gas delivery system 12. The pressure of gas input 18 is preferably at least the highest pressure desired in gas delivery system 12.

Gas delivery system 12 has a low-pressure subsystem 20 and a high-pressure subsystem 22 coupled to gas input 18. Low-pressure subsystem 20 has a pressure regulator 24 and a pressure sensor 26. Pressure regulator 24 is preferably a programmable low-pressure regulator so that a desired constant pressure may be generated. A suitable range of pressures for pressure regulator is 0 to 10 inches or 0 to 20 inches of water.

High-pressure subsystem 22 has a pressure regulator 28, a pressure delivery source such as a valve 30, and a pressure sensor 32. Pressure regulator 28 is also preferably a programmable pressure regulator having a higher pressure than pressure regulator 24. For example, pressure regulator 28 may have a range of 0 to 30 psi.

Valve 30 may, for example, be a solenoid valve. Valve 30 is coupled to a pulse generator 34 that allows a gas pulse of high pressure to be generated. In the preferred embodiment, pulse generator 34 generates an electrical signal to valve 30 in the form of a pulse to generate a pulse of gas pressure. A second pulse generator 34' may be used to generate an electrical signal to valve 15.

A valve 36 acts as a switch and is used to couple low-pressure subsystem 20 and high-pressure subsystem 22 to fluid reservoir 14.

A computer 38 and a controller 40 are used to control the operation and distribution of gas from gas input 18 to fluid reservoir 14. Although computer 38 and controller 40 are shown as separate components, one skilled in the art would recognize that controller 40 may be integrated into computer 38. Computer 38 has a user input (not shown) that allows the microfluidic system 10 to be controlled according to various parameters. That is, the various pressures desired at pressure regulators 24, 28 and the desired timing of pulse generators 34, 34' may be controlled by computer 38 and controller 40. Computer 38 and controller 40 use feedback from pressure sensors 26, 32 to control the operation of gas delivery system 12. Computer 38 and controller 40 are also coupled to valves 15, 30 so that the low-pressure subsystem 20 or high-pressure subsystem 22 may be coupled to flu d reservoir 14. When controlling valve 15, the fluid itself is controlled rather than the gas delivery source as with valve 30. Valves 15, 30 may be used in the alternative or in conjunction. When used in conjunction, valve 30 pressurizes the system, while valve 15 controls fluid delivery.

Figure 4:
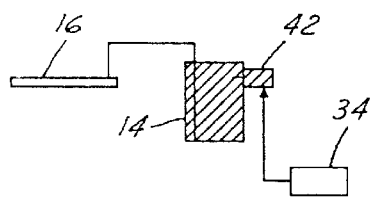
FIG. 4 is a partial schematic view of an alternative embodiment of the fluid reservoir of FIG. 3.

Referring now to FIG. 4, a pressure delivery source such as a piezoelectric device 42 may be used in place of solenoid valve 30 so that a pressure pulse may be applied to fluid reservoir 14. As illustrated, a pressure pulse may be applied to the gas above the fluid. One skilled in the art would recognize that the piezoelectric device 42 could be coupled directly to the fluid.

Figure 5:
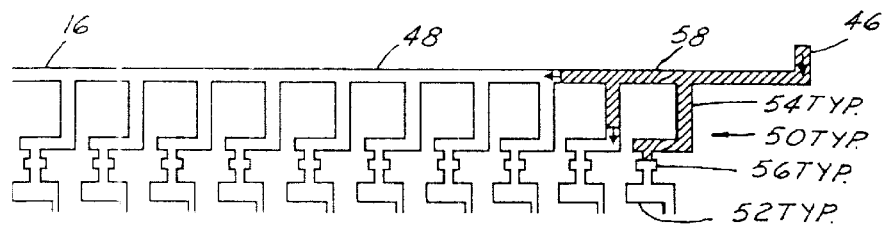
FIG. 5 is a cutaway view of microfluidic capillaries being filled according to the present invention.

Referring now to FIG. 5, the operation of the microfluidic distribution system 10 is best described with respect to microfluidic device 16. Microfluidic device 16 has an input 46 that is coupled to fluid reservoir 14. Input 46 is coupled to a main channel 48. Main channel 48 has various branches 50 that fluidically couple main channel 48 to reaction well 52. As is shown, ten reaction wells 52 are illustrated. However, various numbers of reaction wells 52 may be employed. The number of reaction wells 52 could approach 10,000 all of which may be coupled to a single fluid delivery system. The wells may also be grouped together and be serviced by several fluid delivery systems.

Branches 50 have a cell feed 54 and a capillary break 56. As shown, fluid 58 has entered through input 46 and has filled the first branches 50 up to capillary break 56. Capillary break 56 due to surface tension prevents fluid below a certain pressure from flowing through break 56. Once a sufficient pressure is reached, fluid flows through break. The flow of fluid 58 is initiated through computer 38 and controller 40 through low-pressure subsystem 20. Low pressure subsystem 20 provides a regulated constant gas pressure from gas input 18 into fluid reservoir 14 that displaces fluid from fluid reservoir 14 into fluid input 46. The low pressure supplied by low-pressure subsystem 20 is insufficient to break the capillary break 56.

Figure 6:
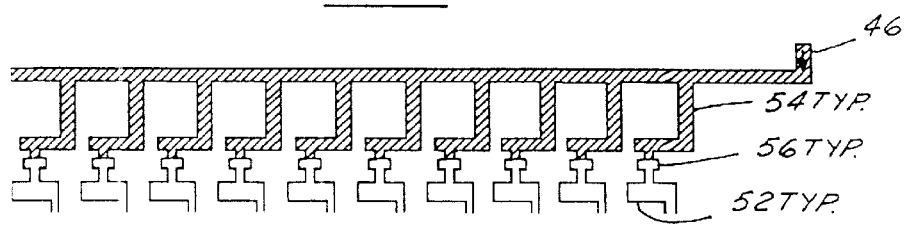
FIG. 6 is a cutaway view such as that shown in FIG. 5 having capillaries filled to an initial state.

Referring now to FIG. 6, each branch 50 is shown filled up to capillary break 56. Branches 50 are filled sequentially from the closest to fluid input 46 to the most distant from fluid input 46.

Figure 7:
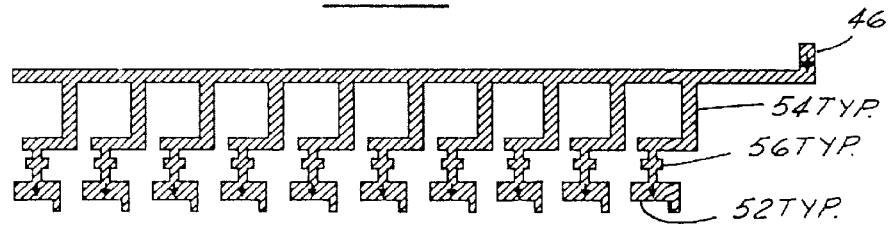
FIG. 7 is a cutaway view such as that shown in FIG. 5 with a reaction well in a full state.

Referring now to FIG. 7, fluid has now entered reaction well 52. High-pressure subsystem 22 is used to overcome capillary break 56 by delivering a high-pressure gas pulse to fluid reservoir 14. The high-pressure gas pulse displaces a high-pressure fluid pulse from fluid reservoir 14 into microfluidic device 16 through input 46. The high-pressure pulse is large enough to overcome the capillary break 56 in each of branches 50.

Figure 8:
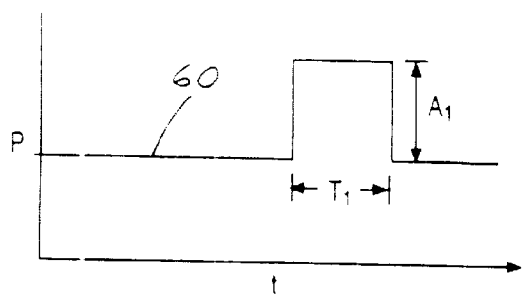
FIG. 8 is a pressure versus time plot of a pressure pulse formed according to the present invention.

Referring now to FIG. 8, a suitable high-pressure pulse is illustrated. In one constructed embodiment, a pulse 60 having amplitude $A_1$ of 1 psi and a period length $T_1$ of 115 milliseconds was applied to fluid input 46. By varying the pulse widths, the amount of fluid displaced may be changed.

A second pulse may be applied to displace fluid from a well on a chip. The magnitude of the pulses can be used to meter fluid to and from well to provide metered filling as well as metered dispensing.

Figure 9:
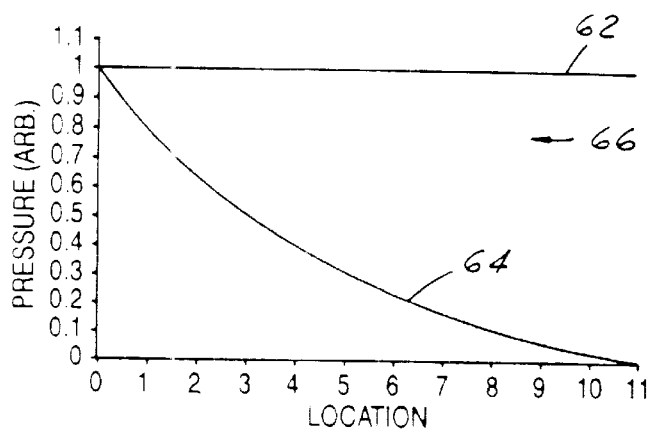
FIG. 9 is a plot of an upper limit pressure drop and a lower limit pressure drop along a micro channel.

Referring now to FIG. 9, a plot of the upper limit pressure drops along main channel 48 for stagnant fluid flow is shown by line 62. As will be evident to those skilled in the art, the pressure along main channel 48 decreases as the distance from fluid input 46 increases due to the pressure drop from each branch 50. Line 64 represents the pressure drop along main channel 48. The locations along the x-axis 1 through 11 correspond to the branches 50. Line 64 corresponds to the lower limit pressure drop along main channel 48 for a fully developed fluid flow. Area 66 between line 62 and line 64 corresponds to a transient region of the operation of a microfluidic device 16. As the distance from fluid input 46 increases, the lower limit line 64 approaches zero.

Figure 10:
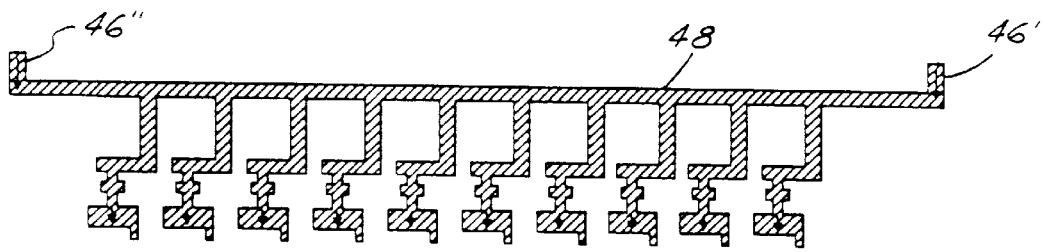
FIG. 10 is a two-sided pressure head system operated in a similar manner to that described with respect to FIG. 3.

Referring now to FIG. 10, to overcome the decrease in pressure due to the distance from the input and the pressure drop due to each branch 50, a first input 46' and a second input 46" may be coupled to main channel 48 at opposite ends.

Figure 11:
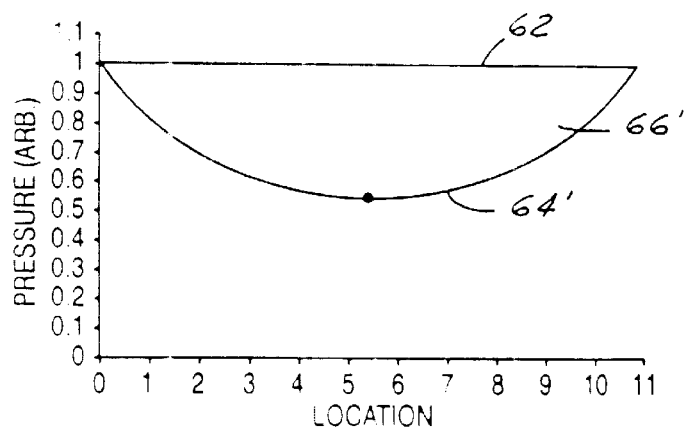
FIG. 11 is a plot of pressure versus location showing upper limit pressure drop and lower limit pressure drop along the microfluidic structure of FIG. 10.

Referring now to FIG. 11, transient area 66' has been reduced significantly by adding a second fluid input 46". The lower limit pressure drop denoted by line 64' may be reduced to about 50 percent of the upper limit line 62' compared to almost zero with a single input as illustrated in FIG. 9.

While particular embodiments of the invention have been shown and described, numerous variations and alternate embodiments will occur to those skilled in the art. Accordingly, it is intended that the invention be limited only in terms of the appended claims.

What is claimed is:

1. A microfluidic fluid delivery system comprising:
    a microfluidic device having,
        a fluid input;
        a fluid reservoir coupled to said fluid input; and
        a pulse generator generating an electrical pulse; and
    a gas pressure delivery source coupled to said pulse generator and said fluid reservoir, said gas pressure delivery source controlling a gas pressure pulse in response to said electrical pulse, said gas pressure pulse displacing fluid from said fluid reservoir into said fluid input.

2. A microfluidic fluid delivery system as recited in claim 1 wherein said gas delivery pressure delivery source comprises a high-pressure subsystem and a low-pressure subsystem.

3. A microfluidic fluid delivery system as recited in claim 2 wherein said high pressure subsystem comprises a first pressure regulator coupled to a gas input.

4. A microfluidic fluid delivery system as recited in claim 3 wherein said first pressure regulator comprises a programmable pressure regulator.

5. A microfluidic fluid delivery system as recited in claim 1 wherein said low pressure subsystem comprises a second pressure regulator coupled to a gas input.

6. A microfluidic fluid delivery system as recited in claim 3 wherein said second pressure regulator comprises a programmable pressure regulator.

7. A microfluidic fluid delivery system as recited in claim 1 wherein said pressure delivery source comprises a solenoid valve.

8. A microfluidic fluid delivery system as recited in claim 1 wherein said microfluidic device further comprising a main channel coupled to said fluid input, said main channel having a plurality of branches extending therefrom.

9. A microfluidic fluid delivery system as recited in claim 8 wherein each of said branches have a channel feed, a capillary break and a reaction well.

10. A microfluidic fluid delivery system as recited in claim 1 wherein said microfluidic device comprises a second fluid input coupled to said fluid reservoir.

11. A microfluidic fluid delivery system as recited in claim 8 wherein said main channel has a first end and a second end, said plurality of branches disposed between said first end and said second end.

12. A microfluidic fluid delivery system as recited in claim 1 wherein said gas pressure delivery source comprises a piezoelectric device.

13. A microfluidic system comprising:
   a fluid reservoir;
   a microfluidic chip having a first fluid input channel coupled to the fluid reservoir and a plurality of wells coupled to said first fluid input channel;
   a gas input fluidically coupled to said fluid reservoir;
   a low-pressure distribution system coupled to said gas input providing a low-pressure to said fluid reservoir;
   a high-pressure distribution system coupled to said gas input to provide a pulsed high pressure to said fluid reservoir;
   a first pulse generator generating a first electrical pulse;
   a first valve electrically coupled to said first pressure generator, and fluidically coupled to said high-pressure distribution system and said gas input, said first valve operated in response to said first electrical pulse;
   a controller coupled to said first valve and said second valve, said controller selectively coupling said second valve to said low-pressure fluid distribution system to supply fluid to fill said first fluid input channel of said microfluidic chip and selectively coupling said second valve to said high-pressure fluid distribution system to supply, by said high-pressure gas pulse, fluid to fill said plurality of wells of said microfluidic chip.

14. A microfluidic fluid delivery system as recited in claim 13 wherein said high pressure distribution system comprises a first pressure regulator coupled to said gas input.

15. A microfluidic fluid delivery system as recited in claim 14 wherein said high pressure distribution system comprises a first pressure sensor electrically coupled to said controller and fluidically coupled between said first regulator and said second valve.

16. A microfluidic fluid delivery system as recited in claim 13 wherein said low pressure distribution system comprises a second pressure regulator coupled to said gas input.

17. A microfluidic fluid delivery system as recited in claim 16 wherein said low pressure distribution system comprises a second pressure sensor electrically coupled to said controller and fluidically coupled between said second regulator and said second valve.

18. A microfluidic fluid delivery system as recited in claim 13 wherein said first valve comprises a solenoid valve.

19. A microfluidic fluid delivery system as recited in claim 13 wherein said microfluidic device comprises a second fluid input coupled to said reservoir.

* * * * *